US012082892B2

(12) United States Patent
Tojo et al.

(10) Patent No.: US 12,082,892 B2
(45) Date of Patent: Sep. 10, 2024

(54) SURGICAL ROBOT AND METHOD FOR DISPLAYING IMAGE OF PATIENT PLACED ON SURGICAL TABLE

(71) Applicant: KAWASAKI JUKOGYO KABUSHIKI KAISHA, Kobe (JP)

(72) Inventors: Tsuyoshi Tojo, Ibaraki (JP); Yuji Kishida, Kobe (JP); Takeshi Kurihara, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 535 days.

(21) Appl. No.: 17/225,197

(22) Filed: Apr. 8, 2021

(65) Prior Publication Data

US 2021/0315647 A1 Oct. 14, 2021

(30) Foreign Application Priority Data

Apr. 9, 2020 (JP) .................. 2020-070407

(51) Int. Cl.
  *A61B 34/30* (2016.01)
  *A61B 34/00* (2016.01)
  *A61B 90/00* (2016.01)
  *A61B 90/50* (2016.01)

(52) U.S. Cl.
  CPC ............. *A61B 34/30* (2016.02); *A61B 34/25* (2016.02); *A61B 34/70* (2016.02); *A61B 90/36* (2016.02); *A61B 90/361* (2016.02); *A61B 90/50* (2016.02); *A61B 2034/301* (2016.02); *A61B 2034/302* (2016.02); *A61B 2034/742* (2016.02); *A61B 2090/364* (2016.02); *A61B 2560/0437* (2013.01)

(58) Field of Classification Search
  CPC ......... A61B 34/00; A61B 34/30; A61B 34/70; A61B 90/00; A61B 90/50; A61B 90/36; A61B 2034/742; A61B 19/201; A61B 19/203; A61B 19/5244
  See application file for complete search history.

(56) References Cited

U.S. PATENT DOCUMENTS

| | | | |
|---|---|---|---|
| 8,251,891 B2 * | 8/2012 | Moskowitz | A61B 1/05 606/1 |
| 2017/0172674 A1 | 6/2017 | Hanuschik et al. | |
| 2018/0296285 A1 * | 10/2018 | Simi | A61B 34/71 |
| 2019/0201145 A1 * | 7/2019 | Shelton, IV | A61B 90/90 |
| 2020/0054406 A1 | 2/2020 | Hanuschik et al. | |

FOREIGN PATENT DOCUMENTS

| | | |
|---|---|---|
| JP | 2017-515522 A | 6/2017 |
| JP | 2018-534099 A | 11/2018 |
| WO | 2017/064301 A1 | 4/2017 |
| WO | 2019/177711 A1 | 9/2019 |

* cited by examiner

*Primary Examiner* — Vi X Nguyen
(74) *Attorney, Agent, or Firm* — METROLEX IP LAW GROUP, PLLC; Robert L. Scott, Esq.

(57) ABSTRACT

A surgical robot includes an arm base mover configured to move an arm base configured to support a plurality of arms, an imaging device provided on the arm base, the imaging device being configured to image a patient placed on a surgical table, and a display configured to display, in real time, the patient imaged by the imaging device.

19 Claims, 13 Drawing Sheets

SURGICAL ROBOT AND METHOD FOR DISPLAYING IMAGE OF PATIENT PLACED ON SURGICAL TABLE

CROSS-REFERENCE TO RELATED APPLICATION

The priority application number JP2020-070407, Surgical Robot and Method for Positioning Surgical Robot, Apr. 9, 2020, Tsuyoshi Tojo, Yuji Kishida, and Takeshi Kurihara, upon which this patent application is based, is hereby incorporated by reference.

BACKGROUND OF THE INVENTION

Field of the Invention

The present disclosure relates to a surgical robot and a method for displaying an image of a patient placed on a surgical table.

Description of the Background Art

Conventionally, a surgical robot aligned with a patient is known. Such a surgical robot is disclosed in Japanese Translation of PCT International Application Publication No 2017-515522.

Japanese Translation of PCT International Application Publication No 2017-515522 discloses a teleoperational assembly (surgical robot) including a plurality of arms to which medical instruments such as endoscopes are attached. The teleoperational assembly includes a base and a telescoping support column attached to the base. The telescoping support column is provided along a vertical direction. Furthermore, a telescoping boom is provided so as to extend in a horizontal direction from the telescoping support column. The plurality of arms are attached to an orienting platform provided at the tip end of the telescoping boom via a plurality of support beams.

The teleoperational assembly disclosed in Japanese Translation of PCT International Application Publication No 2017-515522 is configured to irradiate a patient (such as a patient placed on a surgical table) with a reference laser beam from the teleoperational assembly. An operator (such as a nurse or a technician) who moves the teleoperational assembly moves the entire teleoperational assembly according to a guided setup screen prompt and a voice prompt as shown in FIG. 13 such that the plurality of arms are placed along the reference laser beam directly radiated to the patient. Thus, the operator is attempting to align the teleoperational assembly with the patient.

However, in a case of the teleoperational assembly disclosed in Japanese Translation of PCT International Application Publication No 2017-515522, the touchpad only displays an image related to the next operation procedure, and thus the operator (such as a nurse or a technician) who moves the teleoperational assembly cannot align the teleoperational assembly while checking the patient's condition.

SUMMARY OF THE INVENTION

The present disclosure is intended to solve the above problem. The present disclosure aims to provide a surgical robot and a method for displaying an image of a patient placed on a surgical table that each enable an operator who aligns the surgical robot with the patient to align the surgical robot with the patient while checking the patient's condition.

In order to attain the aforementioned object, a surgical robot according to a first aspect of the present disclosure includes a plurality of arms each configured to allow a medical device to be attached thereto, an arm base configured to support the plurality of arms, an arm base mover configured to move the arm base, a medical cart configured to move the arm base mover, an imaging device provided on the arm base, the imaging device being configured to image a patient placed on a surgical table, and a display configured to display, in real time, the patient imaged by the imaging device.

In the surgical robot according to the first aspect of the present disclosure, as described above, the patient imaged by the imaging device is displayed on the display, and the arm base can be aligned with a surgical location in the patient placed on the surgical table on the display while the condition of the patient displayed on the display is checked. Accordingly, an operator (such as a nurse or a technician) can move the medical cart while checking the condition of the patient displayed on the display.

A method for displaying, on a display of a surgical robot, an image of a patient placed on a surgical table, the surgical robot including a plurality of arms each configured to allow a medical device to be attached thereto and an arm base configured to support the plurality of arms, according to a second aspect of the present disclosure includes imaging a patient placed on a surgical table by an imaging device provided on the arm base, and displaying the patient imaged by the imaging device on the display in real time.

As described above, the method for displaying the image of the patient placed on the surgical table according to the second aspect of the present disclosure includes displaying the patient imaged by the imaging device on the display in real time. Accordingly, an operator (such as a nurse or a technician) can move the medical cart so as to align a trocar displayed on the display and a mark with each other while checking the condition of the patient displayed on the display.

According to the present disclosure, as described above, the operator can align the surgical robot with the patient while checking the patient's condition.

The foregoing and other objects, features, aspects and advantages of the present disclosure will become more apparent from the following detailed description of the present disclosure when taken in conjunction with the accompanying drawings.

DESCRIPTION OF THE PREFERRED EMBODIMENTS

Figure 1:
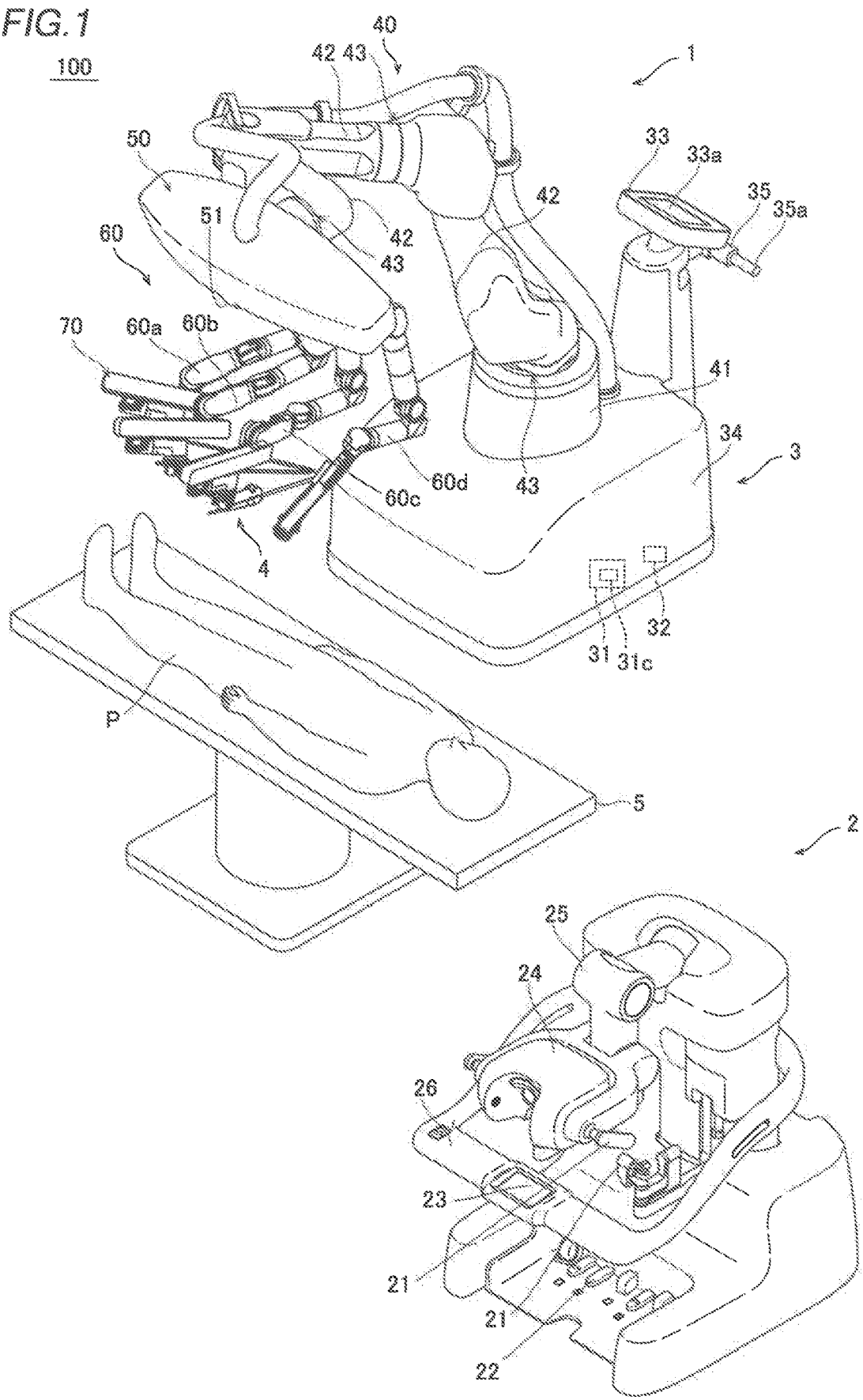
FIG. 1 is a diagram showing the configuration of a surgical system according to an embodiment of the present disclosure.

An embodiment of the present disclosure is hereinafter described with reference to the drawings.

The configuration of a surgical system 100 according this embodiment is now described with reference to FIGS. 1 to 19. The surgical system 100 includes a medical manipulator 1 that is a patient P-side device and a remote operation device 2 that is an operator-side device configured to operate the medical manipulator 1. The medical manipulator 1 includes a medical cart 3, and is configured to be movable. The remote operation device 2 is spaced apart from the medical manipulator 1, and the medical manipulator 1 is configured to be remotely operated by the remote operation device 2. A surgeon inputs a command to the remote operation device 2 to cause the medical manipulator 1 to perform a desired operation. The remote operation device 2 transmits the input command to the medical manipulator 1. The medical manipulator 1 operates based on the received command. The medical manipulator 1 is arranged in an operating room that is a sterilized sterile field. The medical manipulator 1 is an example of a "surgical robot" in the claims.

The remote operation device 2 is arranged inside or outside the operating room, for example. The remote operation device 2 includes operation manipulator arms 21, operation pedals 22, a touch panel 23, a monitor 24, a support arm 25, and a support bar 26. The operation manipulator arms 21 define operation handles for the surgeon to input commands. The monitor 24 is a scope-type display that displays an image captured by an endoscope 6. The support arm 25 supports the monitor 24 so as to align the height of the monitor 24 with the height of the surgeon's face. The touch panel 23 is arranged on the support bar 26. The surgeon's head is detected by a sensor (not shown) provided in the vicinity of the monitor 24 such that the medical manipulator 1 can be operated by the remote operation device 2. The surgeon operates the operation manipulator arms 21 and the operation pedals 22 while visually recognizing an affected area on the monitor 24. Thus, a command is input to the remote operation device 2. The command input to the remote operation device 2 is transmitted to the medical manipulator 1.

The medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote operation device 2.

The medical cart 3 includes an input 33. The input 33 is configured to receive operations to move a positioner 40, an arm base 50, and a plurality of arms 60 or change their postures mainly in order to prepare for surgery before the surgery. The positioner 40 is an example of an "arm base mover" in the claims.

Figure 2:
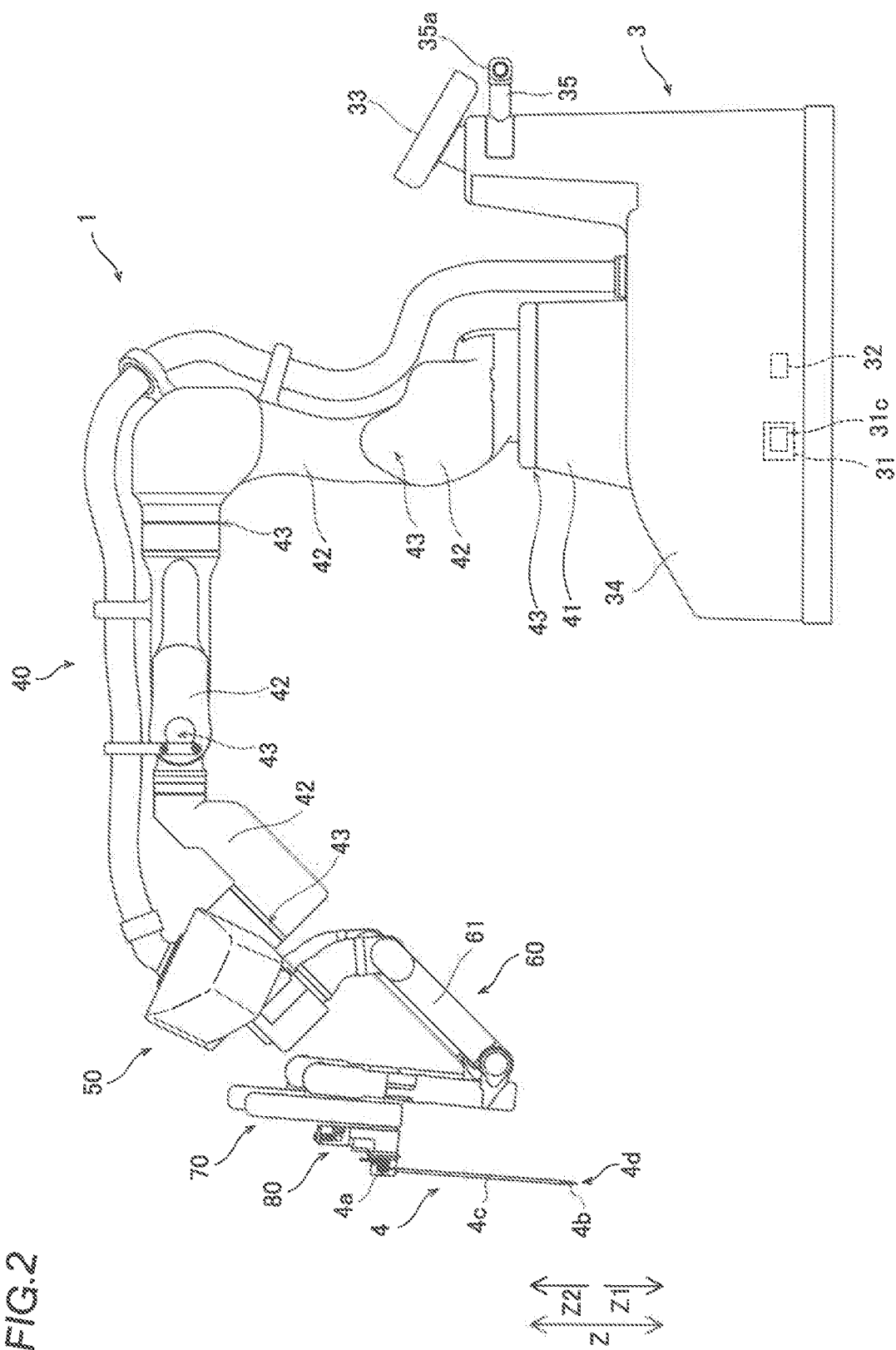
FIG. 2 is a diagram showing the configuration of a medical manipulator according to the embodiment of the present disclosure.

As shown in FIGS. 1 and 2, the medical manipulator 1 is arranged in the operating room. The medical manipulator 1 includes the medical cart 3, the positioner 40, the arm base 50, and the plurality of arms 60. The arm base 50 is attached to the tip end of the positioner 40. The arm base 50 has a relatively long rod shape (long shape). The bases of the plurality of arms 60 are attached to the arm base 50. Each of the plurality of arms 60 is configured to be able to take a folded posture (stored posture). The arm base 50 and the plurality of arms 60 are covered with sterile drapes (not shown) and used.

In this embodiment, the arm base 50 includes an imaging device 51. The imaging device 51 is provided to align the arm base 50 and the arms 60 with the patient P who is placed on a surgical table 5 and has the trocars T inserted into their body surface S.

The positioner 40 includes a 7-axis articulated robot, for example. The positioner 40 is arranged on a casing 34 of the medical cart 3. The positioner 40 moves the arm base 50. Specifically, the positioner 40 is configured to move the position of the arm base 50 three-dimensionally.

The positioner 40 includes a base 41 and a plurality of links 42 coupled to the base 41. The plurality of links 42 are coupled to each other by joints 43.

As shown in FIG. 1, a medical device 4 is attached to the tip end of each of the plurality of arms 60. The medical device 4 includes a replaceable instrument (see FIG. 2) or the endoscope 6 (see FIG. 7), for example.

As shown in FIG. 2, the instrument as the medical device 4 includes a driven unit 4a driven by a servomotor M2 provided in a holder 71 of each of the arms 60. An end effector 4b is provided at the tip end of the instrument. The end effector 4b includes a pair of forceps, a pair of scissors, a grasper, a needle holder, a microdissector, a stable applier, a tacker, a suction cleaning tool, a snare wire, a clip applier, etc. as instruments having joints. The end effector 4b includes a cutting blade, a cautery probe, a washer, a catheter, a suction orifice, etc. as instruments having no joint. The medical device 4 includes a shaft 4c that connects the driven unit 4a to the end effector 4b. The driven unit 4a, the shaft 4c, and the end effector 4b are arranged along a Z direction.

Figure 3:
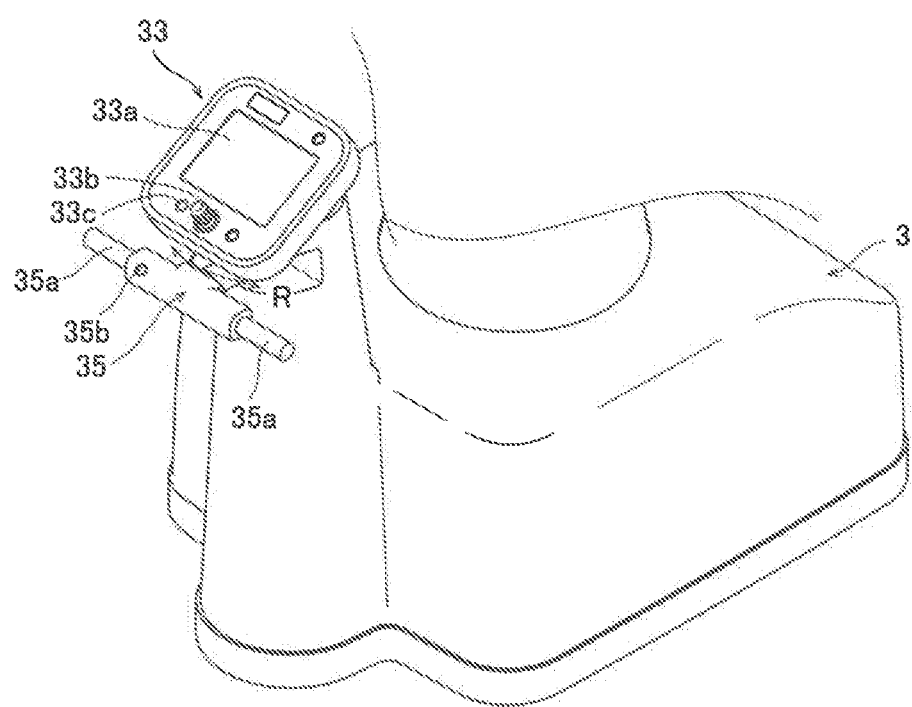
FIG. 3 is a perspective view showing the configuration of a medical cart according to the embodiment of the present disclosure.
Figure 4:
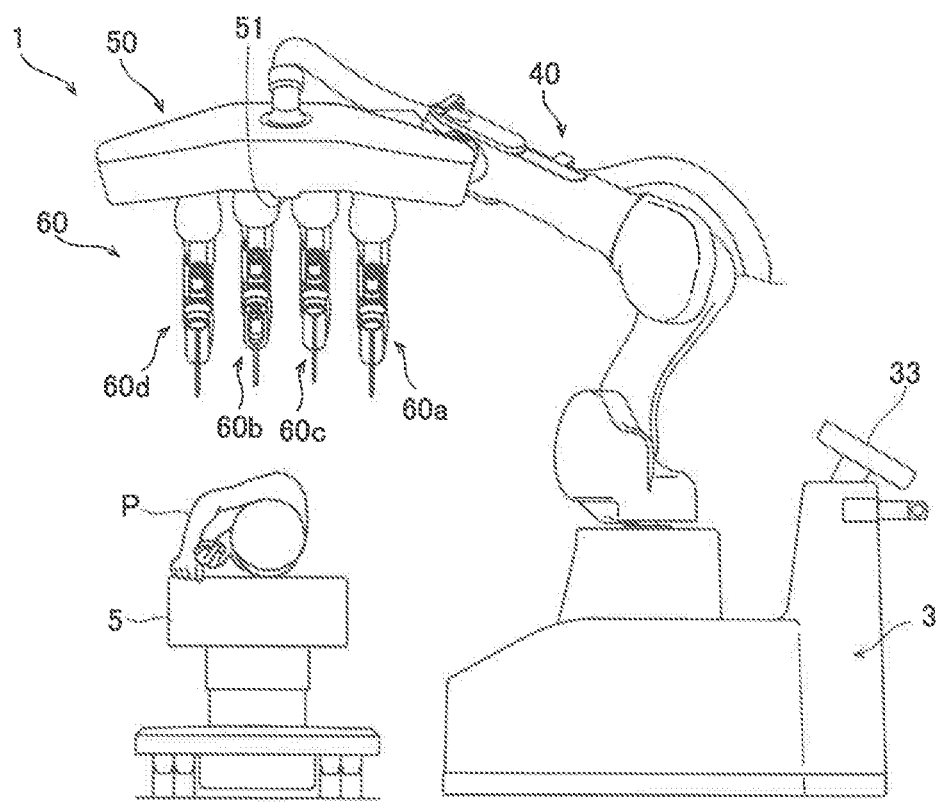
FIG. 4 is a diagram showing a state in which the medical manipulator is moved (rolled in) with respect to a patient.
Figure 5:
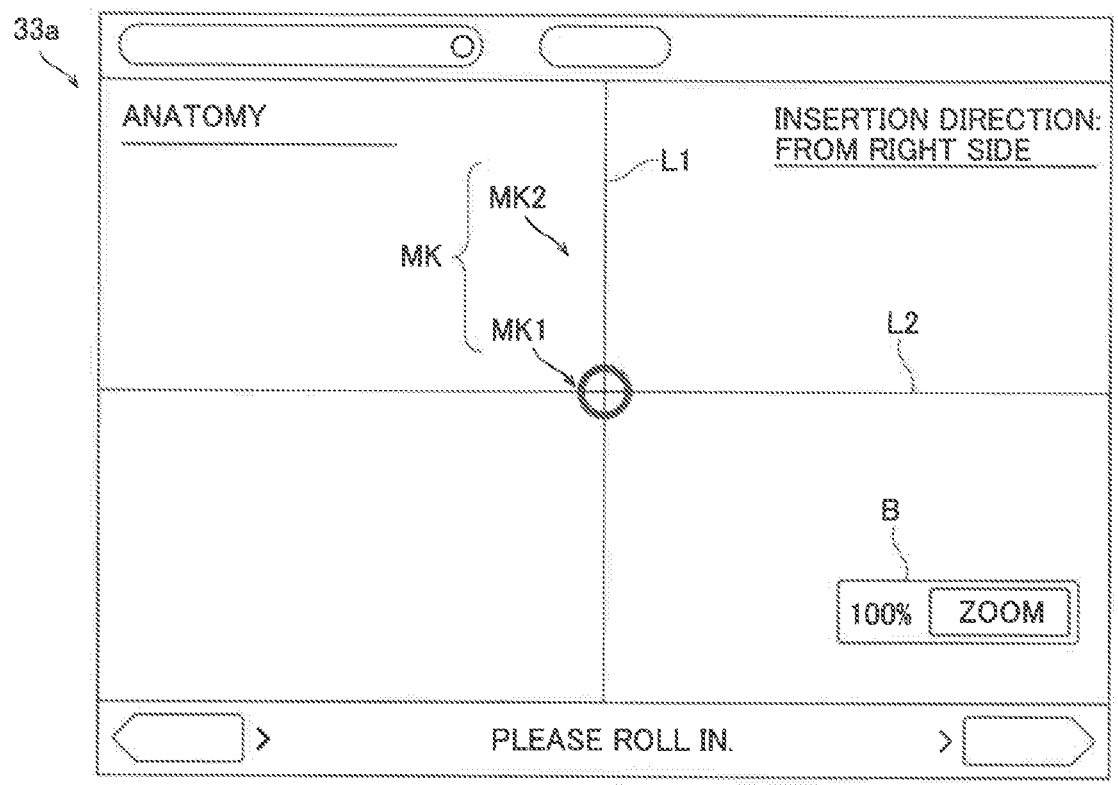
FIG. 5 is a diagram showing marks displayed on a display.
Figure 6:
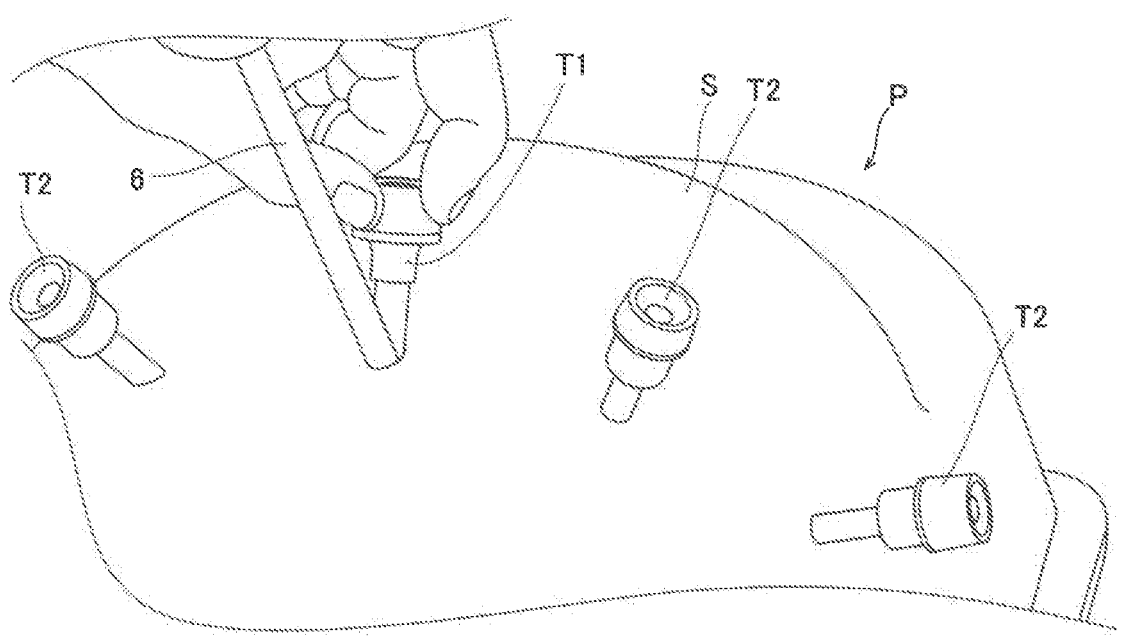
FIG. 6 is a diagram showing trocars inserted into a patient's body surface.
Figure 7:
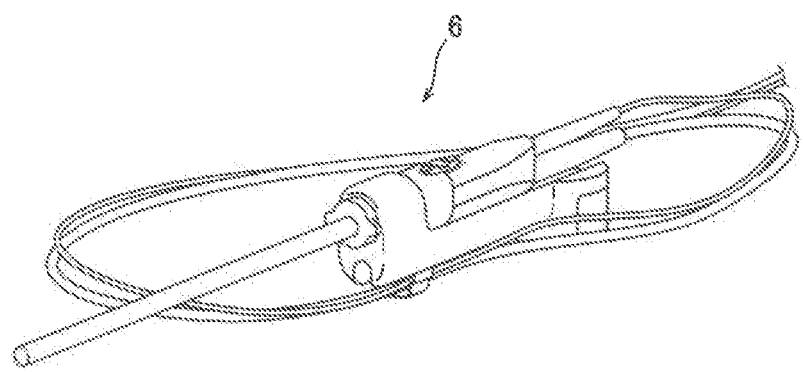
FIG. 7 is a diagram showing an endoscope.

In this embodiment, as shown in FIGS. 3 and 4, the medical cart 3 (input 33) includes a display 33a. The display 33a is configured to display the patient P imaged by the imaging device 51 in real time. As shown in FIG. 5 (and FIGS. 18 and 19), on the display 33a, an image of the patient P captured by the imaging device 51 and marks MK configured to align the arm base 50 with the patient P are superimposed and displayed. Specifically, on the display 33a, an image of the trocars T (see FIG. 6) for inserting the endoscope 6 from the body surface S of the patient P captured the imaging device 51 and the marks MK configured to align the arm base 50 with the trocars T are superimposed and displayed. The marks MK displayed on the display 33a are aligned, on the display 33a, with the trocars T displayed on the display 33a such that the arms 60 are aligned with a surgical location in the patient P placed on the surgical table 5.

The image of the patient P (trocars T) displayed on the display 33a is an image actually captured by the imaging device 51, and the marks MK are graphical user interface (GUI) images generated by the controller 31 and are stored in the storage 32. The controller 31 is equipped with an image processing circuit 31c that displays an image obtained from the imaging device 51 on the display 33a. The image processing circuit 31c using a field programmable gate array (FPGA) mounted on the controller 31 synthesizes and displays the image of the patient P (trocars T) actually captured by the imaging device 51 and stored in the storage 32 and the marks MK of the GUI images on the display 33a in real time with a delay that people do not recognize. The image processing circuit 31c may include an application specific integrated circuit (ASIC) or a system on a chip (SoC), for example, other than the field programmable gate array (FPGA).

Specifically, in this embodiment, the trocars T includes a first trocar T1 into which the endoscope 6 is inserted and second trocars T2 into which the medical devices 4 other than the endoscope 6 are inserted. The marks MK displayed on the display 33a include a first mark MK1 aligned with the first trocar T1 on the display 33a and a second mark MK2 aligned with the second trocars T2 on the display 33a. More specifically, the first mark MK1 is displayed on a substantially central portion of the display 33a and has a substantially circular shape. The second mark MK2 has a cross shape centered on the substantially circular first mark MK1 (intersects at the center of the substantially circular first mark MK1).

In this embodiment, the size of the substantially circular first mark MK1 is larger than the size of the first trocar T1 displayed on the display 33a. Specifically, the diameter of the substantially circular first mark MK1 is larger than the diameter of the first trocar T1 having a substantially circular cross-section.

In this embodiment, a plurality of second trocars T2 are provided on the body surface S of the patient P. The plurality of second trocars T2 are arranged on a substantially straight line. The trocars T are arranged in the order of the second trocar T2, the first trocar T1, the second trocar T2, and the second trocar T2 so as to correspond to a plurality of (four) arms 60.

In this embodiment, the display 33a has a substantially rectangular shape. For example, the display 33a has a horizontally long rectangular shape as viewed from an operator. The cross-shaped second mark MK2 includes a substantially linear first line L1 provided along the longitudinal direction of the substantially rectangular display 33a, and a substantially linear second line L2 provided along the transverse direction of the substantially rectangular display 33a. The medical manipulator 1 is configured such that the plurality of second trocars T2 are aligned along the first line L1 or the second line L2 on the display 33a.

In this embodiment, the display of the first line L1 and the second line L2 on the display 33a is fixed on the display 33a. The display 33a is fixed to the medical cart 3. Thus, a direction along the first line L1 corresponds to the moving direction (forward-rearward direction) of the medical cart 3. An image on the display 33a on which the patient P is displayed changes with movement of the arm base 50 (imaging device 51) or movement of the medical cart 3.

In this embodiment, a magnification change button B is provided to enlarge or reduce an image of the first mark MK1 together with the image of the patient P displayed on the display 33a. The magnification change button B is displayed on the touch panel. When the magnification change button B is pressed, the magnification percentage of an image is changed in a loop of 100%, 200%, 400%, 100%, and 200%. When the magnification percentage of the image is 100%, the end of the surgical table 5 and a nearby assistant and nurse are displayed on the display 33a.

In this embodiment, the first trocar T1 displayed on the display 33a and the first mark MK1 are aligned with each other on the display 33a, and the second trocars T2 displayed on the display 33a and the second mark MK2 are aligned with each other on the display 33a such that the arms 60 are aligned with the surgical location in the patient P placed on the surgical table 5. The details of alignment of the arms 60 with the surgical location in the patient P (roll-in of the medical manipulator 1) are described below.

In this embodiment, as shown in FIG. 3, a joystick 33b for operating movement of the positioner 40 is provided in the vicinity of the display 33a of the medical cart 3. The positioner 40 can be operated three-dimensionally by selecting an operation mode displayed on the display 33a and operating the joystick 33b. At the time of roll-in, the joystick 33b is operated such that the positioner 40 is moved so as to move the arm base 50 on a two-dimensional plane. On the display 33a, the trocars T displayed on the display 33a and the marks MK are aligned with each other. Specifically, the joystick 33b is provided at a substantially central portion of the display 33a in the transverse direction and below the display 33a on the input 33. The joystick 33b is an example of a "first operation unit" in the claims.

In this embodiment, an enable switch 33c for allowing or disallowing movement of the positioner 40 is provided in the vicinity of the joystick 33b of the medical cart 3. The joystick 33b is operated while the enable switch 33c is pressed to allow the positioner 40 to move such that the positioner 40 is moved. Specifically, the enable switch 33c is provided below the display 33a and adjacent to the joystick 33b on the input 33. The enable switch 33c is an example of a "first enable switch" in the claims.

In this embodiment, a handle 35 for operating movement of the medical cart 3 is provided in the vicinity of the display 33a of the medical cart 3. The handle 35 includes throttles 35a that are gripped and rotated by the operator (such as a nurse or a technician) to operate movement of the medical cart 3. Specifically, the handle 35 is arranged below the input 33. A pair of throttles 35a are provided at both ends of the handle 35. The throttles 35a are rotated from the front side to the rear side such that the medical cart 3 moves forward. The throttles 35a are rotated from the rear side to the front side such that the medical cart 3 moves rearward. The speed of the medical cart 3 is changed according to the amount of rotation of the throttles 35a. The handle 35 is configured to be rotatable to the left and right (R direction), and the moving direction of the medical cart 3 is changed with rotation of the handle 35. The handle 35 is an example of a "second operation unit" in the claims.

In this embodiment, an enable switch 35b for allowing or disallowing movement of the medical cart 3 is provided in the vicinity of the handle 35 of the medical cart 3. The throttles 35a of the handle 35 are operated in a state in which the enable switch 35b is pressed and the medical cart 3 is allowed to move such that the medical cart 3 is moved. Specifically, the enable switch 35b is provided adjacent to one of the pair of throttles 35a on the handle 35. The enable switch 35b is an example of a "second enable switch" in the claims.

In this embodiment, while the trocars T displayed on the display 33a and the marks MK are aligned with each other on the display 33a, the positioner 40 is controlled such that the arm base 50 is moved in order for the imaging device 51 to image a region vertically therebelow. This control is performed by the controller 31 that controls the operation of the medical manipulator 1.

The configuration of the arms 60 is now described in detail.

Figure 8:
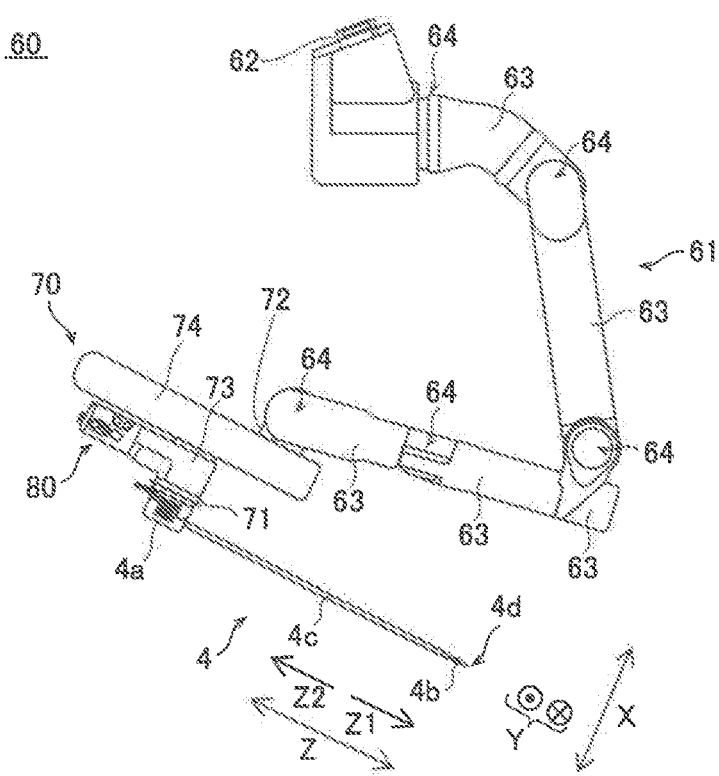
FIG. 8 is a diagram showing the configuration of an arm of the medical manipulator according to the embodiment of the present disclosure.

As shown in FIG. 8, each of the arms 60 includes an arm portion 61 (a base 62, links 63, and joints 64) and a translation mechanism 70 provided at the tip end of the arm portion 61. The arms 60 are configured to be able to three-dimensionally move the tip end sides with respect to the base sides (arm base 50) of the arms 60. The plurality of arms 60 have the same configuration as each other.

The translation mechanism 70 is provided on the tip end side of the arm portion 61, and the medical device 4 is attached thereto. The translation mechanism 70 translates the medical device 4 in a direction in which the medical device 4 is inserted into the patient P. Furthermore, the translation mechanism 70 is configured to translate the medical device 4 relative to the arm portion 61. Specifically, the translation mechanism 70 includes the holder 71 that holds the medical device 4. The servomotor M2 (see FIG. 14) is housed in the holder 71. The servomotor M2 is configured to rotate a rotating body provided in the driven unit 4a of the medical device 4. The rotating body of the driven unit 4a is rotated such that the end effector 4b is operated.

The arms 60 are configured to be removable from the arm base 50.

The arm portion 61 includes a 7-axis articulated robot arm. The arm portion 61 includes the base 62 configured to attach the arm portion 61 to the arm base 50, and a plurality of links 63 coupled to the base 62. The plurality of links 63 are coupled to each other by the joints 64.

The translation mechanism 70 is configured to translate the medical device 4 attached to the holder 71 along the Z direction (a direction in which the shaft 4c extends) by translating the holder 71 along the Z direction. Specifically, the translation mechanism 70 includes a base end side link 72 connected to the tip end of the arm portion 61, a tip end side link 73, and a coupling link 74 provided between the base end side link 72 and the tip end side link 73. The holder 71 is provided on the tip end side link 73.

The coupling link 74 of the translation mechanism 70 is configured as a double speed mechanism that moves the tip end side link 73 relative to the base end side link 72 along the Z direction. The tip end side link 73 is moved along the Z direction relative to the base end side link 72 such that the medical device 4 provided on the holder 71 is translated along the Z direction. The tip end of the arm portion 61 is connected to the base end side link 72 so as to rotate the base end side link 72 about a Y direction orthogonal to the Z direction.

As shown in FIG. 1, the endoscope 6 is attached to one (an arm 60b, for example) of the plurality of arms 60, and the medical devices 4 other than the endoscope 6 are attached to the remaining arms 60 (arms 60a, 60c, and 60d, for example).

Figure 9:
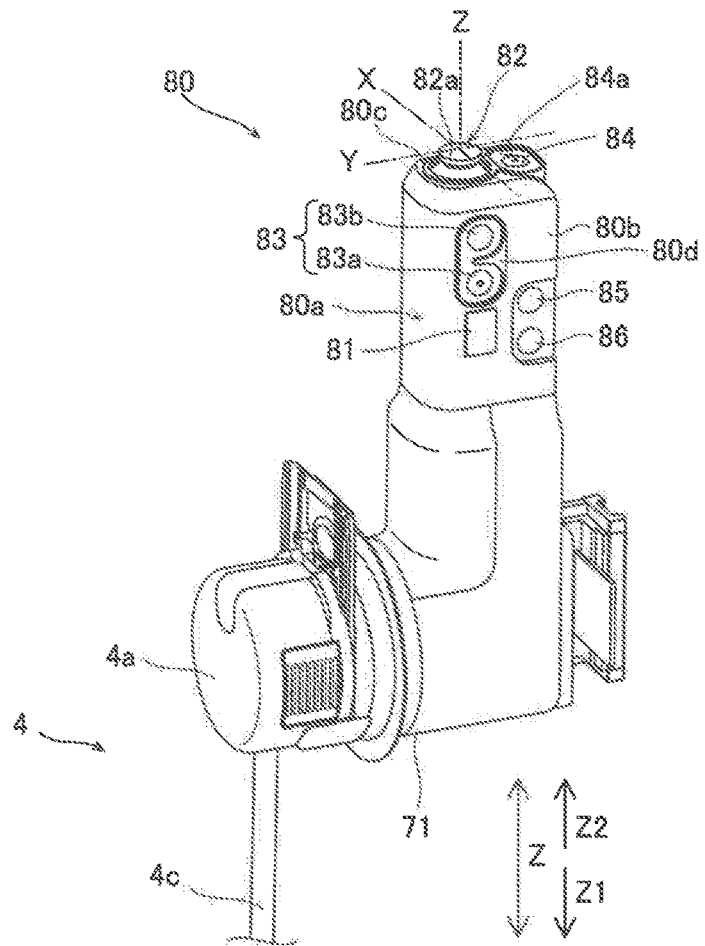
FIG. 9 is a perspective view showing the configuration of an operation unit of the medical manipulator according to the embodiment of the present disclosure.

As shown in FIG. 9, the medical manipulator 1 includes an operation unit 80 attached to each of the arms 60 to operate the arm 60. The operation unit 80 includes enable switches 81, a joystick 82, and switch units 83. The enable switches 81 allow or disallow movement of the arm 60 through the joystick 82 and the switch units 83. The enable switches 81 get into a state of allowing movement of the medical device 4 by the arm 60 when the operator (such as a nurse or an assistant) grasps and presses the operation unit 80.

Specifically, the enable switches 81 are push-button switches pressed by the operator's fingers. The enable switches 81 are pressed such that it becomes possible to perform a control to energize servomotors M1 to M3 (perform a control to drive the servomotors M1 to M3). That is, it becomes possible to perform a control to move the arm 60 only while the enable switches 81 are pressed.

Figure 11:
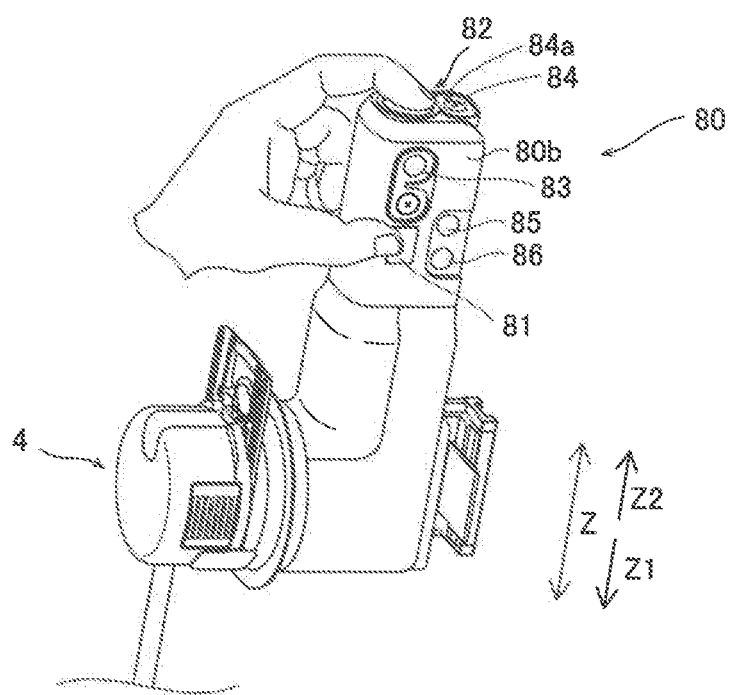
FIG. 11 is a diagram showing a state in which an operator grasps the operation unit of the medical manipulator according to the embodiment of the present disclosure.

As shown in FIG. 11, the operator tilts the joystick 82 with their finger such that the joystick 82 is operated. The arm 60 is controlled to be moved according to a direction in which the joystick 82 is tilted and an angle at which the joystick 82 is tilted. The operator brings their finger into contact with the tip end 82a of the joystick 82, moves their finger, and tilts the joystick 82 to operate the joystick 82. Only while the enable switches 81 are pressed, a signal input based on the operation of the joystick 82 is received. That is, when the enable switches 81 are not pressed, the arm 60 is not moved even when the joystick 82 is operated.

Figure 10:
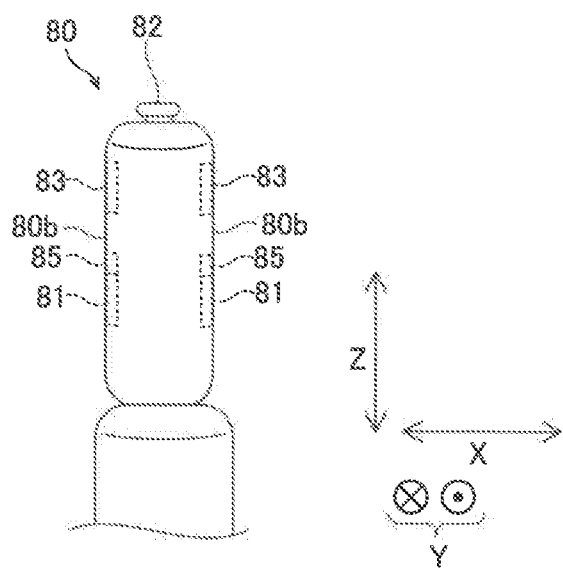
FIG. 10 is a side view showing the configuration of the operation unit of the medical manipulator according to the embodiment of the present disclosure.

As shown in FIGS. 9 and 10, the joystick 82 is provided on an end face 80c of the operation unit 80 that intersects with an outer peripheral surface 80a. The operator can operate the joystick 82 with their finger while grasping the outer peripheral surface 80a of the operation unit 80 and pressing the enable switches 81 so as to allow movement of the arm 60. For example, as shown in FIG. 11, the operator operates the joystick 82 provided on the end face 80c of the operation unit 80 with their index finger, for example, while pressing a pair of enable switches 81 provided on the outer peripheral surface 80a of the operation unit 80 with their thumb and middle finger, for example. Thus, substantially constant distances between the operator's thumb and middle finger that grasp the operation unit 80 and the operator's index finger that operates the joystick 82 can be easily maintained. Which fingers are used to operate the enable switches 81 and the joystick 82 is not limited to the above example. Movement of the arm 60 may be allowed while only one of the pair of enable switches 81 is pressed.

The joystick 82 is configured to operate movement of the medical device 4 by the arm 60 such that the tip end 4d (see FIG. 8) of the medical device 4 moves on a predetermined plane. The operation unit 80 includes the switch units 83 configured to operate movement of the medical device 4 by the arm 60 such that the tip end 4d of the medical device 4 moves along the longitudinal direction of the medical device 4 orthogonal to the predetermined plane. The predetermined plane on which the tip end 4d of the medical device 4 moves refers to a plane (an X-Y plane in FIG. 9) parallel to the end face 80c of the operation unit 80. The longitudinal direction of the medical device 4 orthogonal to the predetermined plane refers to the Z direction orthogonal to the X-Y plane in FIG. 9. Coordinates represented by an X-axis, a Y-axis, and a Z-axis in FIG. 9 are referred to as a tool coordinate system (or a base coordinate system). When the switch units 83 are pressed while the enable switches 81 are pressed (while movement of the medical device 4 by the arm 60 is allowed), the tip end 4d of the medical device 4 is moved along the longitudinal direction of the medical device 4.

Each of the switch units 83 includes a switch 83a configured to move the tip end 4d of the medical device 4 in the direction in which the medical device 4 is inserted into the patient P along the longitudinal direction of the medical device 4, and a switch 83b configured to move the tip end 4d of the medical device 4 in a direction opposite to the direction in which the medical device 4 is inserted into the patient P. Both the switch 83a and the switch 83b are push-button switches.

As shown in FIG. 9, the operation unit 80 includes pivot buttons 85 each configured to teach a pivot position PP that serves as a fulcrum (see FIG. 13) for movement of the medical device 4 attached to the arm 60. The pivot buttons 85 are provided adjacent to the enable switches 81 on a surface 80b of the operation unit 80. When the pivot buttons 85 are pressed, the pivot position PP is taught.

Figure 12:
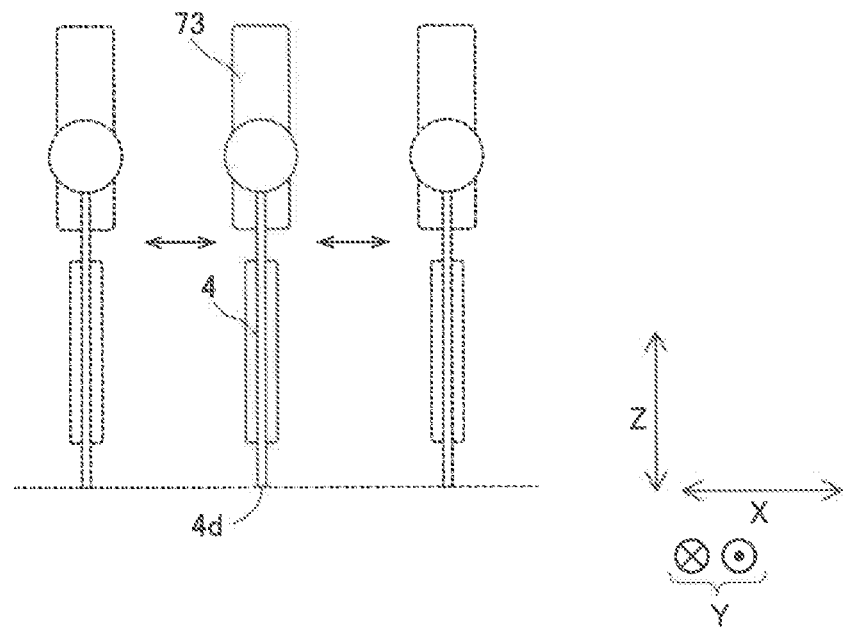
FIG. 12 is a diagram for illustrating translation of the arm.
Figure 13:
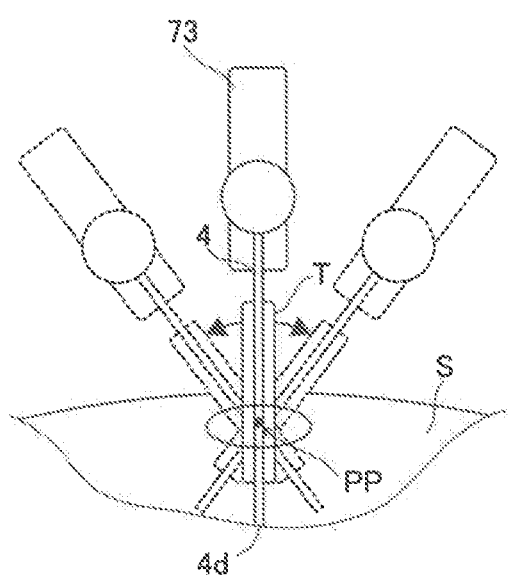
FIG. 13 is a diagram for illustrating rotation of the arm.

As shown in FIG. 9, the operation unit 80 includes a mode switching button 84 configured to switch between a mode for translating the medical device 4 attached to the arm 60 (see FIG. 12) and a mode for rotating the medical device 4 (see FIG. 13). In the operation unit 80, the mode switching button 84 is arranged in the vicinity of the joystick 82. Specifically, on the end face 80c of the operation unit 80, the mode switching button 84 is provided adjacent to the joystick 82. The mode switching button 84 is a push-button switch. Furthermore, a mode indicator 84a is provided in the vicinity of the mode switching button 84. The mode indicator 84a indicates a switched mode. Specifically, the mode indicator 84a is turned on (rotation mode) or off (translation mode) such that a current mode (translation mode or rotation mode) is indicated.

As shown in FIG. 12, in the mode for translating the arm 60, the arm 60 is moved such that the tip end 4d of the medical device 4 moves on the X-Y plane. As shown in FIG. 13, in the mode for rotating the arm 60, when the pivot position PP is not taught, the arm 60 is moved such that the medical device 4 rotates about the end effector 4b, and when the pivot position PP is taught, the arm 60 is moved such that the medical device 4 rotates about the pivot position PP as a fulcrum. The medical device 4 is rotated while the shaft 4c of the medical device 4 is inserted into the trocar T.

As shown in FIG. 8, the operation unit 80 is provided on the translation mechanism 70. The operation unit 80 is attached to the translation mechanism 70 so as to be adjacent to the medical device 4 attached to the translation mechanism 70. Specifically, the operation unit 80 is attached to the tip end side link 73 of the translation mechanism 70. The operation unit 80 is arranged adjacent to the driven unit 4a of the medical device 4.

Figure 14:
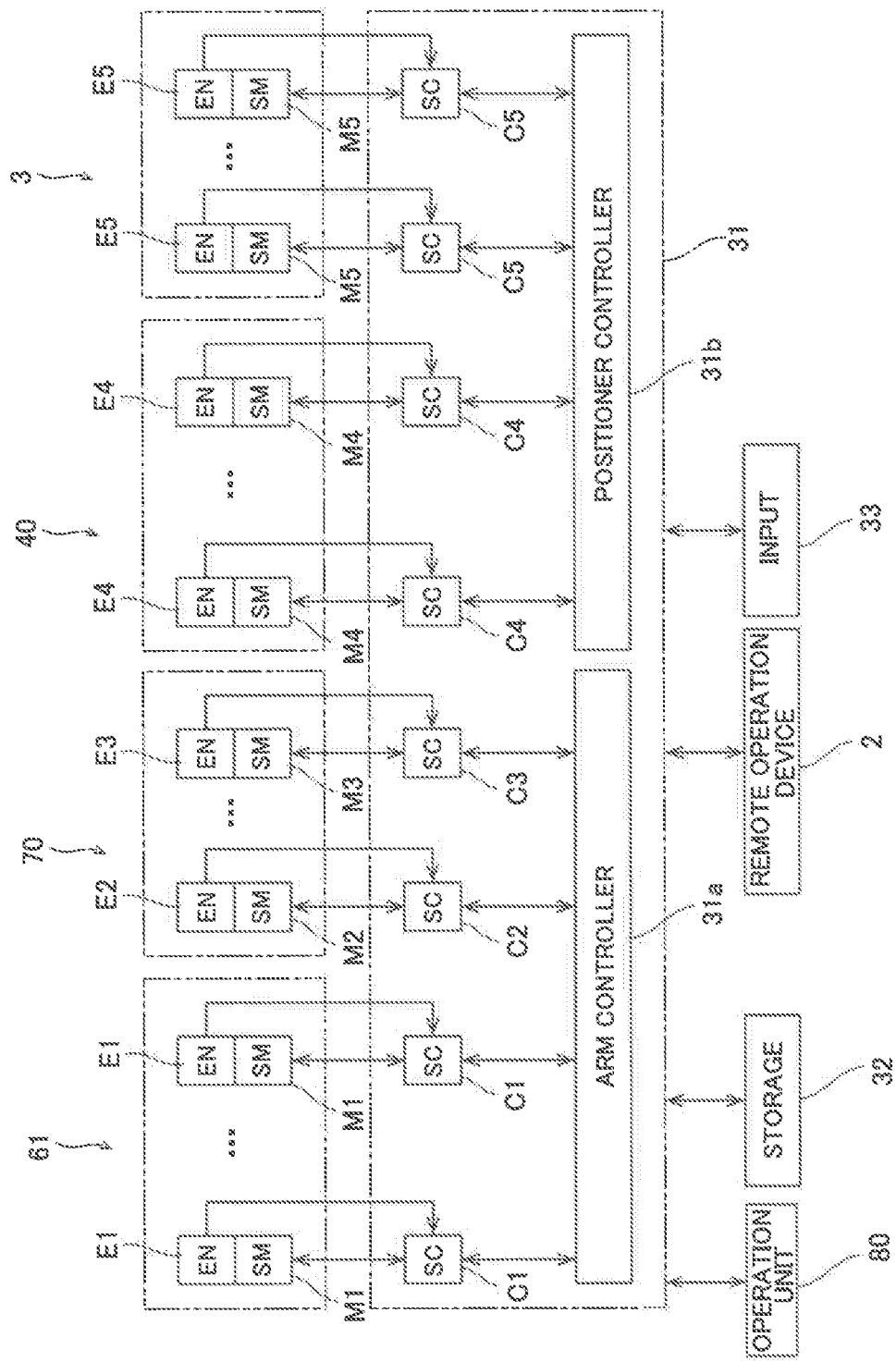
FIG. 14 is a block diagram showing the configuration of a controller of the medical manipulator according to the embodiment of the present disclosure.
Figure 15:
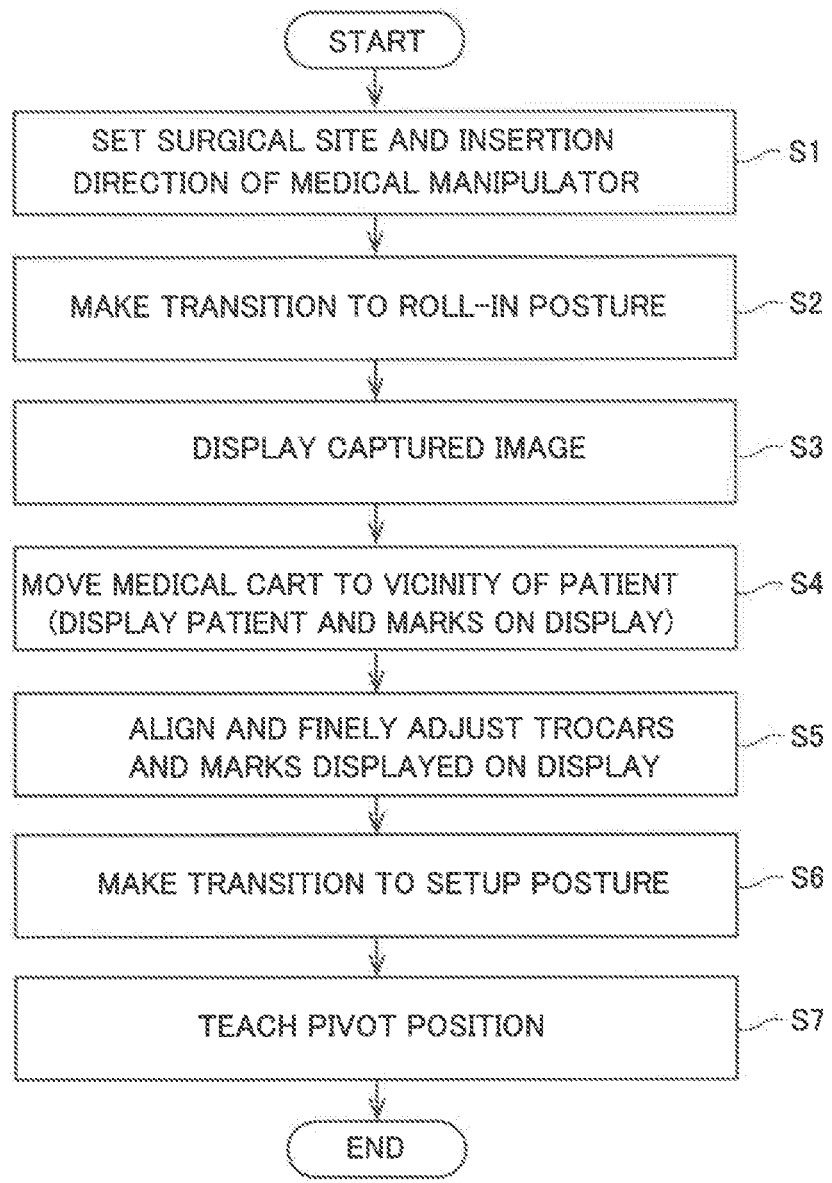
FIG. 15 is a flowchart for illustrating a method for displaying an image of the patient placed on a surgical table according to the embodiment of the present disclosure.

As shown in FIG. 14, the arm 60 includes a plurality of servomotors M1, encoders E1, and speed reducers (not shown) so as to correspond to a plurality of joints 64 of the arm portion 61. The encoders E1 are configured to detect the rotation angles of the servomotors M1. The speed reducers are configured to slow down rotation of the servomotors M1 to increase the torques.

As shown in FIG. 14, the translation mechanism 70 includes the servomotor M2 configured to rotate the rotating body provided in the driven unit 4a of the medical device 4, the servomotor M3 configured to translate the medical device 4, encoders E2 and E3, and speed reducers (not shown). The encoders E2 and E3 are configured to detect the rotation angles of the servomotors M2 and M3, respectively. The speed reducers are configured to slow down rotation of the servomotors M2 and M3 to increase the torques.

The positioner 40 includes a plurality of servomotors M4, encoders E4, and speed reducers (not shown) so as to correspond to a plurality of joints 43 of the positioner 40. The encoders E4 are configured to detect the rotation angles of the servomotors M4. The speed reducers are configured to slow down rotation of the servomotors M4 to increase the torques.

The medical cart 3 includes servomotors M5 configured to drive a plurality of front wheels (not shown) of the medical cart 3, respectively, encoders E5, and speed reducers (not shown). The encoders E5 are configured to detect the rotation angles of the servomotors M5. The speed reducers are configured to slow down rotation of the servomotors M5 to increase the torques.

The controller 31 of the medical cart 3 includes an arm controller 31a that controls movement of the plurality of arms 60 based on commands, and a positioner controller 31b that controls movement of the positioner 40 and driving of the front wheels (not shown) of the medical cart 3 based on commands. Servo controllers C1 configured to control the servomotors M1 configured to drive the arm 60 are electrically connected to the arm controller 31a. The encoders E1 configured to detect the rotation angles of the servomotors M1 are electrically connected to the servo controllers C1.

A servo controller C2 configured to control the servomotor M2 configured to drive the medical device 4 is electrically connected to the arm controller 31a. The encoder E2 configured to detect the rotation angle of the servomotor M2 is electrically connected to the servo controller C2. A servo controller C3 configured to control the servomotor M3 configured to translate the translation mechanism 70 is electrically connected to the arm controller 31a. The encoder E3 configured to detect the rotation angle of the servomotor M3 is electrically connected to the servo controller C3.

An operation command input to the remote operation device 2 is input to the arm controller 31a. The arm controller 31a generates position commands based on the input operation command and the rotation angles detected by the encoders E1 (E2 or E3), and outputs the position commands to the servo controllers C1 (C2 or C3). The servo controllers C1 (C2 or C3) generate torque commands based on the position commands input from the arm controller 31a and the rotation angles detected by the encoders E1 (E2 or E3), and output the torque commands to the servomotors M1 (M2 or M3). Thus, the arm 60 is moved according to the operation command input to the remote operation device 2.

The controller 31 (arm controller 31a) is configured to operate the arm 60 based on an input signal from the joystick 82 of the operation unit 80. Specifically, the arm controller 31a generates position commands based on the input signal (operation command) input from the joystick 82 and the rotation angles detected by the encoders E1, and outputs the position commands to the servo controllers C1. The servo controllers C1 generate torque commands based on the position commands input from the arm controller 31a and the rotation angles detected by the encoders E1, and output the torque commands to the servomotors M1. Thus, the arm 60 is moved according to the operation command input to the joystick 82.

The controller 31 (arm controller 31a) is configured to operate the arm 60 based on an input signal from each of the switch units 83 of the operation unit 80. Specifically, the arm controller 31a generates a position command(s) based on the input signal (operation command) input from each of the switch units 83 and the rotation angle(s) detected by the encoders E1 or the encoder E3, and outputs the position command(s) to the servo controllers C1 or the servo controller C3. The servo controllers C1 or the servo controller C3 generates a torque command(s) based on the position command(s) input from the arm controller 31a and the rotation angle(s) detected by the encoders E1 or the encoder E3, and output(s) the torque command(s) to the servomotors M1 or the servomotor M3. Thus, the arm 60 is moved according to the operation command input to each of the switch units 83.

As shown in FIG. 14, servo controllers C4 configured to control the servomotors M4 that move the positioner 40 are electrically connected to the positioner controller 31b. The encoders E4 configured to detect the rotation angles of the servomotors M4 are electrically connected to the servo controllers C4. Servo controllers C5 configured to control the servomotors M5 that drive the front wheels (not shown) of the medical cart 3 are electrically connected to the positioner controller 31b. The encoders E5 configured to detect the rotation angles of the servomotors M5 are electrically connected to the servo controllers C5.

An operation command regarding preparation position setting, for example, is input from the input 33 to the positioner controller 31b. The positioner controller 31b generates position commands based on the operation command input from the input 33 and the rotation angles detected by the encoders E4, and outputs the position commands to the servo controllers C4. The servo controllers C4 generate torque commands based on the position commands input from the positioner controller 31b and the rotation angles detected by the encoders E4, and output the torque commands to the servomotors M4. Thus, the positioner 40 is moved according to the operation command input to the input 33. Similarly, the positioner controller 31b moves the medical cart 3 based on an operation command from the input 33.

A method for displaying the image of the patient P placed on the surgical table 5 (a method for positioning the medical manipulator 1) is now described. Positioning the medical manipulator 1 refers to aligning the arms 60 with the surgical location in the patient P placed on the surgical table 5. The trocars T (one first trocar T1 and three second trocars T2; see FIG. 6) are inserted in advance into the body surface S of the patient P. The height of the arm base 50 (arms 60) is fixed.

Figure 16:
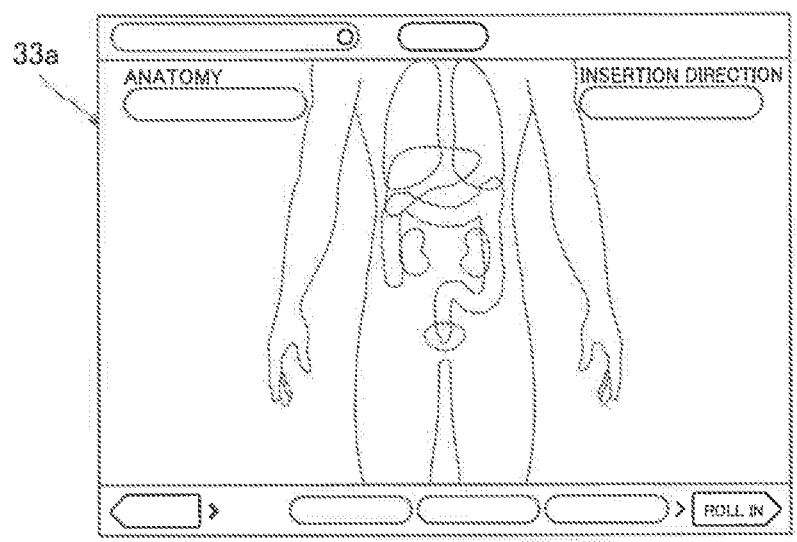
FIG. 16 is a diagram showing the display of the medical cart according to the embodiment of the present disclosure.

First, in step S1 (see FIG. 15), preparation for positioning the medical manipulator 1 is performed. Specifically, as shown in FIG. 16, on the display 33a (touch panel), a surgical site (anatomy: "abdomen", for example) and a direction in which the medical manipulator 1 is inserted into the patient P ("from the right side", for example) are selected.

Then, in step S2, as shown in FIG. 16, a "roll in" button displayed on the display 33a is pressed. Thus, a roll-in mode is set, and the movement operation of the arm base 50 and the arms 60 is controlled such that the medical manipulator 1 takes a roll-in posture. The roll-in posture refers to a posture in which each arm 60 is folded so as not to interfere with the patient P when the arm 60 is positioned above the patient P by movement of the medical manipulator 1, a posture in which the arm base 50 is arranged by the positioner 40 such that the imaging device 51 provided on the arm base 50 can image the region vertically therebelow, and a posture in which the arm base 50 is arranged by the positioner 40 such that the orientation of the arm base 50 corresponds to the arrangement direction of the arms 60 determined based on the information on the surgical site and the information on the insertion direction selected in step S1. That is, after the "roll in" button displayed on the display 33a is pressed such that a transition to the roll-in mode is made, the joystick 33b is operated while the enable switch 33c is pressed to allow the positioner 40 to move such that the controller 31 moves the positioner 40 and each arm 60 such that the medical manipulator 1 automatically takes the roll-in posture.

Figure 17:
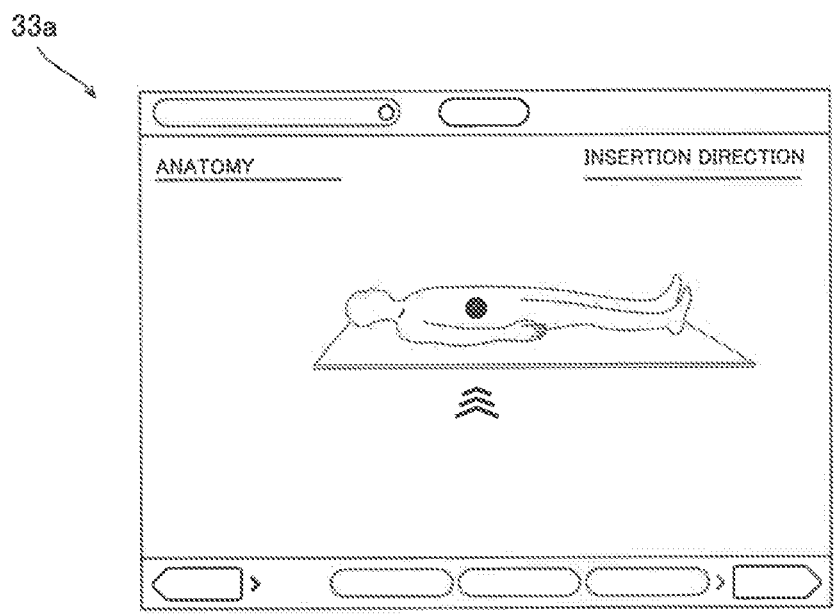
FIG. 17 is another diagram showing the display of the medical cart according to the embodiment of the present disclosure.

Then, in step S3, as shown in FIG. 17, after the movement operation of the arms 60, a screen of the display 33a is switched to an image captured by the imaging device 51. That is, the display of the image captured by the imaging device 51 provided on the arm base 50 is started. Furthermore, the display 33a displays the marks MK (the first mark MK1 and the second mark MK2). In this imaging, a moving image is captured. The positioner 40 is controlled to move the arm base 50 such that the orientation of the arm base 50 corresponds to the arrangement direction of the plurality of arms 60 determined based on an input of the information on the surgical site, an input of the information on the direction in which the medical manipulator 1 is inserted into the patient P, and an input of mode setting for aligning the arm base 50 with the patient P. In the roll-in posture, when the arm base 50 is rotated in a horizontal plane such that the arrangement direction of the arms 60 correspond to the surgical site and the insertion direction selected in step S1, the captured image is corrected to be rotated in a direction opposite to rotation of the arm base 50 and displayed on the display 33a. Thus, the operator (such as a nurse or a technician) can start movement of the medical manipulator 1 while viewing the image of the patient P corrected to an orientation corresponding to the orientation of the operator.

Then, in step S4, the operator operates the handle 35 including the throttles 35a while visually recognizing the display 33a (the image captured by the imaging device 51) such that the medical cart 3 is moved (rolled in) to the vicinity of the patient P placed on the surgical table 5. When the handle 35 is not rotated to the left or right, the first line L1 of the second mark MK2 displayed on the display 33a coincides with the moving direction of the medical cart 3. The display of the first line L1 and the second line L2 on the display 33a is fixed on the display 33a. An image displayed on the display 33a changes with movement of the arm base 50 (imaging device 51) or movement of the medical cart 3.

Figure 18:
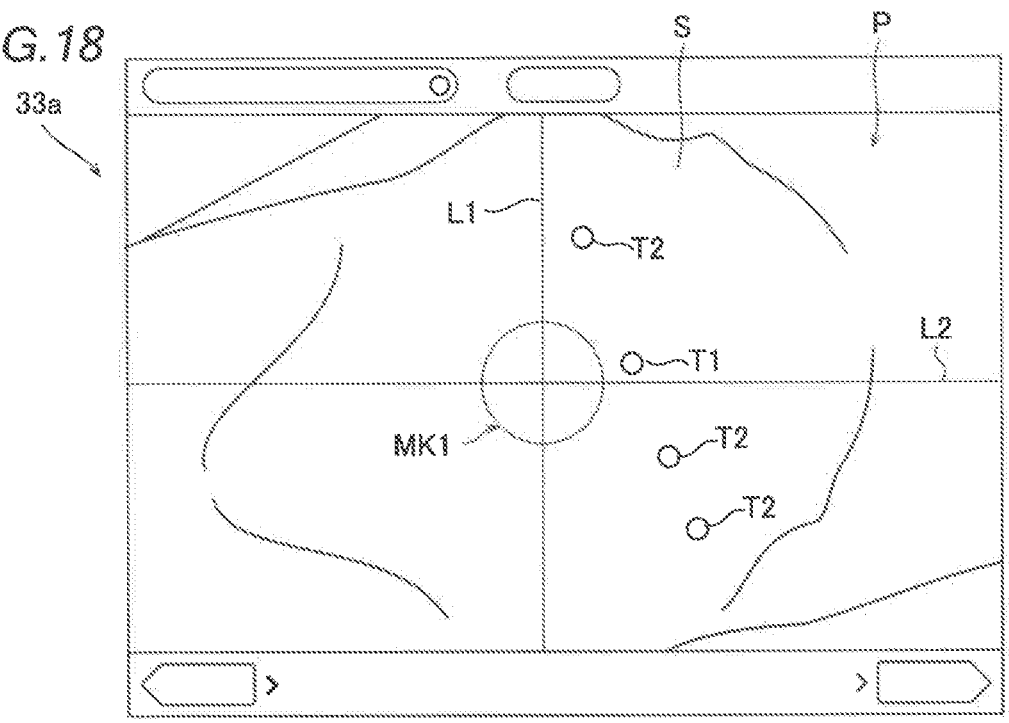
FIG. 18 is a diagram showing alignment between the trocars displayed on the display and the marks.

Then, as shown in FIG. 18, the medical cart 3 is moved to the vicinity of the patient P placed on the surgical table 5 such that the imaging device 51 provided on the arm base 50 images the patient P placed on the surgical table 5 and having the trocars T inserted into their body surface S. Thus, the patient P having the trocars T inserted into their body surface S imaged by the imaging device 51 is displayed on the display 33a. Furthermore, the marks MK aligned with the trocars T displayed on the display 33a are displayed on the display 33a. At this time, the relative positional relationship between the trocars T inserted into the body surface S of the patient P and the marks MK, which changes with movement of the arm base 50 accompanying movement of the medical cart 3, is displayed on the display 33a.

Specifically, on the display 33a, the substantially circular first mark MK1 and the cross-shaped second mark MK2 are displayed in advance. Then, on the display 33a, the body surface S of the patient P imaged by the imaging device 51 is displayed so as to overlap the first mark MK1 and the second mark MK2.

Then, in step S5, the operator operates the handle 35 including the throttles 35a to move the medical cart 3 while visually recognizing the display 33a (the image captured by the imaging device 51) such that the first trocar T1 is arranged inside the substantially circular first mark MK1. In the roll-in posture, the arm base 50 is rotated in the horizontal plane such that the arrangement direction of the arms 60 correspond to the surgical site and the insertion direction selected in step S1, and thus on the display 33*a*, the plurality of second trocars T2 are arranged substantially on the first line L1 or the second line L2 of the second mark MK2 with the first trocar T1 being arranged inside the substantially circular first mark MK1.

In step S5, when the trocars T are misaligned with the first line L1 or the second line L2, the operator operates the joystick 33*b* while pressing the enable switch 33*c* such that the arm base 50 is rotated in the horizontal plane. Thus, the position of the arm base 50 is finely adjusted. The image of the body surface S of the patient P rotates with rotation of the medical cart 3 or the arm base 50. On the other hand, on the display 33*a*, the first mark MK1 and the second mark MK2 are fixed. The magnification change button B is pressed to switch the magnification percentage of the image such that the operator can easily view the image.

Figure 19:
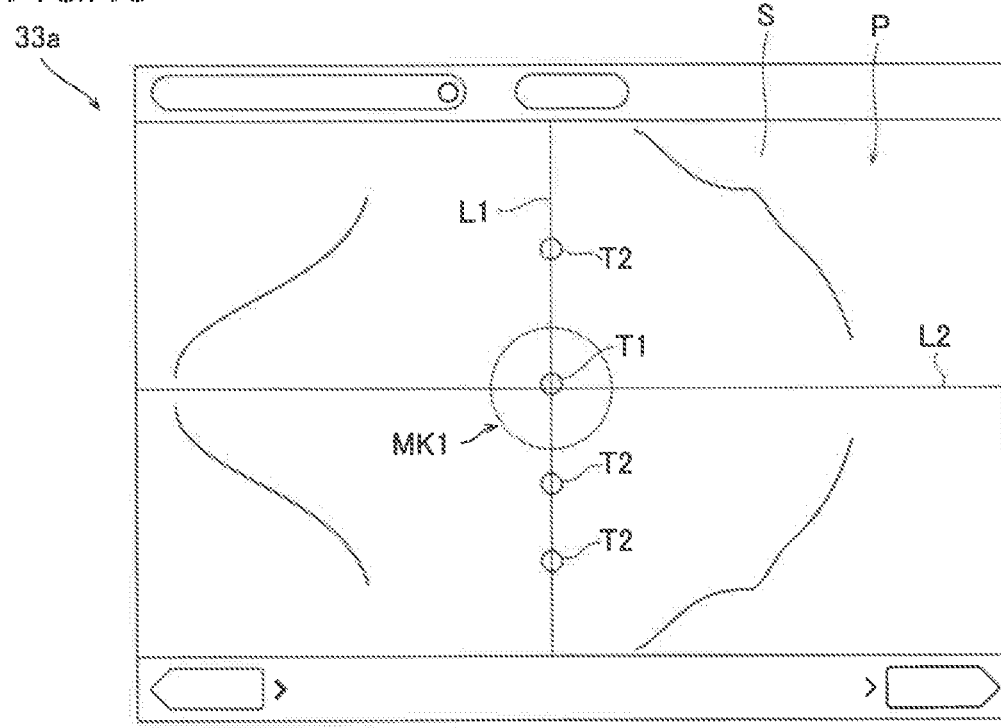
FIG. 19 is another diagram showing alignment between the trocars displayed on the display and the marks.

Then, as shown in FIG. 19, the joystick 33*b* is operated such that the trocars T displayed on the display 33*a* and the marks MK are finely adjusted so as to be aligned with each other on the display 33*a*. Specifically, the position of the arm base 50 is finely adjusted by rotating the arm base 50 in the horizontal plane such that the plurality of second trocars T2 are arranged on the first line L1 or the second line L2 of the second mark MK2 with the first trocar T1 being arranged inside the substantially circular first mark MK1. In FIG. 19, the arm base 50 is rotated such that the plurality of second trocars T2 are arranged on the first line L1. Thus, positioning of the medical manipulator 1 is completed. Depending on surgical technique, the plurality of second trocars T2 do not necessarily need to be arranged on the first line L1 or the second line L2 of the second mark MK2.

Then, in step S6, the plurality of arms 60 transition to a setup posture. The setup posture refers to a posture in which the plurality of arms 60 are further opened (extended) than in the roll-in posture so as to facilitate teaching of the pivot position PP described below. As shown in FIG. 19, after an "arm preparation" button is pressed such that a transition to a setup posture mode is made, the joystick 33*b* is operated while the enable switch 33*c* is pressed to allow the positioner 40 to move such that the controller 31 moves the positioner 40 and the arms 60 to cause the medical manipulator 1 to take the setup posture. After a transition to the setup posture is made, a stabilizer (not shown) mounted on the medical cart 3 is activated when a button for allowing the stabilizer displayed on the touch panel is pressed.

Then, in step S7, the endoscope 6 is attached to the arm 60 corresponding to the first trocar T1, and the pivot position PP is taught. After the teaching of the pivot position PP of the endoscope 6 is completed, the medical devices 4 other than the endoscope 6 are attached, and the pivot positions PP are taught.

In step S5, the medical cart 3 is moved such that the first trocar T1 is arranged inside the first mark MK1, but the medical cart 3 may be moved to a position at which the patient is arranged below the arm base 50 without aligning the first mark MK1 with the first trocar T1. In this case, in step S5, the operator operates the joystick 33*b* while pressing the enable switch 33*c* such that the arm base 50 is rotated and translated in the horizontal plane so as to align the first mark MK1 with the first trocar T1 while the medical manipulator 1 maintains the roll-in posture.

Advantages of this Embodiment

According to this embodiment, the following advantages are achieved.

Advantages of Surgical Robot

According to this embodiment, as described above, the patient P imaged by the imaging device 51 is displayed on the display 33*a*, and the arm base 50 can be aligned with the surgical location in the patient P placed on the surgical table 5 on the display 33*a* while the condition of the patient P displayed on the display 33*a* is checked. Accordingly, the operator (such as a nurse or a technician) can move the medical cart 3 while checking the condition of the patient P displayed on the display 33*a*.

According to this embodiment, as described above, the image of the patient P captured by the imaging device 51 and the marks MK used to align the arm base 50 with the patient P are superimposed and displayed on the display 33*a*. Accordingly, the operator (such as a nurse or a technician) can easily move the medical cart 3 while checking the marks MK superimposed on the image of the patient P.

According to this embodiment, as described above, the image of the trocars T configured to allow the endoscope 6 to be inserted from the body surface S of the patient P captured by the imaging device 51 and the marks MK used to align the arm base 50 with the trocars T are superimposed and displayed on the display 33*a*. Accordingly, the operator (such as a nurse or a technician) can move the medical cart 3 while visually recognizing the display 33*a* provided on the medical cart 3 such that the trocars T displayed on the display 33*a* and the marks MK are aligned with each other.

According to this embodiment, as described above, the arms 60 are aligned with the surgical location in the patient P placed on the surgical table 5 by aligning the trocars T displayed on the display 33*a* with the marks MK. Accordingly, the arms 60 can be aligned with the surgical location with a short movement distance.

According to this embodiment, as described above, the trocars T include the trocar T (first trocar T1) configured to allow the endoscope 6 to be inserted thereinto, and the mark MK displayed on the display 33*a* is aligned with the trocar T (first trocar T1) on the display 33*a*. Accordingly, the mark MK is displayed on the display 33*a* for the first trocar T1 into which the endoscope 6 is inserted, and thus alignment using the endoscope 6 as a reference can be performed.

According to this embodiment, as described above, the trocars T include the first trocar T1 configured to allow the endoscope 6 to be inserted thereinto and the second trocars T2 configured to allow the medical devices 4 other than the endoscope 6 to be inserted thereinto, and the marks MK displayed on the display 33*a* include the first mark MK1 used to align with the first trocar T1 on the display 33*a* and the second mark MK2 used to align with the second trocars T2 on the display 33*a*. Accordingly, the marks MK are separately displayed on the display 33*a* for the first trocar T1 into which the endoscope 6 is inserted and the second trocars T2 into which the medical devices 4 other than the endoscope 6 are inserted, and thus the medical devices 4 other than the endoscope 6 can be aligned using the endoscope 6 as a reference.

According to this embodiment, as described above, the first mark MK1, which has a substantially circular shape, is displayed on the substantially central portion of the display 33*a*, and the second mark MK2 has a cross shape centered on the substantially circular first mark MK1. Generally, one first trocar T1 into which the endoscope 6 is inserted and a plurality of second trocars T2 to which the medical devices 4 other than the endoscope 6 are attached are inserted into the body surface S of the patient P. Furthermore, one first trocar T1 and the plurality of second trocars T2 are arranged substantially linearly. Therefore, with the configuration described above, the first mark MK1 and the second mark MK2 can be easily aligned with one first trocar T1 and the plurality of second trocars T2 arranged substantially linearly, respectively, on the display 33a.

According to this embodiment, as described above, the size of the substantially circular first mark MK1 is larger than the size of the first trocar T1 displayed on the display 33a. Accordingly, even when the sizes of the first trocars T1 are slightly different from each other depending on the types of first trocars T1, the first trocar T1 can be aligned inside the substantially circular first mark MK1.

According to this embodiment, as described above, the plurality of second trocars T2 are provided on the body surface S of patient P, the display 33a has a substantially rectangular shape, the cross-shaped second mark MK2 includes the substantially linear first line L1 provided along the longitudinal direction of the substantially rectangular display 33a, and the substantially linear second line L2 provided along the transverse direction of the substantially rectangular display 33a, and the plurality of second trocars T2 are aligned on the first line L1 or the second line L2 on the display 33a. Accordingly, on the display 33a, the first line L1 or the second line L2 can be easily aligned with the plurality of second trocars T2 generally arranged on a substantially straight line.

According to this embodiment, as described above, the first line L1 and the second line L2 displayed on the display 33a are fixed on the display 33a. Accordingly, the first line L1 provided along the longitudinal direction of the display 33a corresponds to the moving direction of the medical cart 3, and thus the moving direction of the medical cart 3 can be easily recognized.

According to this embodiment, as described above, the first trocar T1 displayed on the display 33a and the first mark MK1 are aligned with each other on the display 33a, and the second trocars T2 displayed on the display 33a and the second mark MK2 are aligned with each other on the display 33a such that the arms 60 are aligned with the surgical location in the patient P placed on the surgical table 5. Accordingly, the trocars T are aligned with both the first mark MK1 and the second mark MK2 on the display 33a, and thus the arms 60 can be more appropriately aligned with the surgical location in the patient P.

According to this embodiment, as described above, the magnification change button B is provided to enlarge or reduce the image of the first mark MK1 together with the image of the patient P displayed on the display 33a. Accordingly, the image displayed on the display 33a can be enlarged such that the operator (such as a nurse or a technician) can easily view the image, and thus it is easy to align the trocars T and the marks MK with each other on the display 33a.

According to this embodiment, as described above, the display 33a includes the touch panel, and the magnification change button B is displayed on the touch panel. Accordingly, the operator (such as a nurse or a technician) can easily enlarge the image displayed on the display 33a simply by touching the magnification change button B on the touch panel.

According to this embodiment, as described above, the medical manipulator 1 includes the joystick 33b provided in the vicinity of the display 33a to operate movement of the positioner 40. Furthermore, the joystick 33b is operated and causes the positioner 40 to move the arm base 50 on the two-dimensional plane, and the trocars T displayed on the display 33a and the marks MK are aligned with each other on the display 33a. Accordingly, the joystick 33b configured to operate movement of the positioner 40 is provided in the vicinity of the display 33a, and thus the operator can operate the joystick 33b while visually recognizing the display 33a.

According to this embodiment, as described above, the medical manipulator 1 includes the enable switch 33c provided in the vicinity of the joystick 33b and configured to allow or disallow movement of the positioner 40. Furthermore, the joystick 33b is operated and causes the positioner 40 to move the arm base while the enable switch 33c is pressed. Accordingly, the enable switch 33c is provided in the vicinity of the joystick 33b, and thus the joystick 33b can be easily operated while the enable switch 33c is pressed.

According to this embodiment, as described above, the joystick 33b is provided in the vicinity of the display 33a. Accordingly, the operator (such as a nurse or a technician) can easily operate the joystick 33b with their finger.

According to this embodiment, as described above, the medical manipulator 1 includes the handle 35 provided in the vicinity of the display 33a to operate movement of the medical cart 3. Accordingly, the handle 35 is provided in the vicinity of the display 33a, and thus the operator can move the arm base 50 by operating the handle 35 while visually recognizing the display 33a.

According to this embodiment, as described above, the handle 35 includes the throttles 35a gripped and rotated by the operator (such as a nurse or a technician) to cause the medical cart 3 to move. Accordingly, the operator can easily operate movement of the medical cart 3 simply by rotating the throttles 35a while visually recognizing the display 33a.

According to this embodiment, as described above, the medical manipulator 1 includes the enable switch 35b provided in the vicinity of the handle 35 and configured to allow or disallow movement of the medical cart 3. Furthermore, the handle 35 is operated and causes the medical cart 3 to move while the enable switch 35b is pressed. Accordingly, the enable switch 35b is provided in the vicinity of the handle 35, and thus the handle 35 can be easily operated while the enable switch 35b is pressed.

According to this embodiment, as described above, the positioner 40 moves the arm base 50 such that the imaging device 51 takes a posture to image the region vertically therebelow based on an input for setting the roll-in mode to align the arm base 50 with the patient P. Accordingly, the relative positional relationship between the arms 60 and the patient P in the horizontal direction can be appropriately adjusted, unlike a case in which the imaging device 51 captures an image along a direction that intersects with a vertical downward direction.

According to this embodiment, as described above, when movement of the arm base 50 includes horizontal rotation of the arm base 50, the image displayed on the display 33a is corrected to be rotated in the direction opposite to rotation of the arm base 50. Accordingly, the image of the patient P can be displayed on the display 33a in the orientation corresponding to the orientation of the operator.

According to this embodiment, as described above, the image processing circuit 31c is mounted on the controller 31, and thus the image captured by the imaging device 51 can be displayed on the display 33a in real time with a delay that people do not recognize. Accordingly, even when performing an operation while viewing the display 33*a*, the operator can roll in the medical manipulator 1 without interference of the medical manipulator 1 with the patient P. The image processing circuit 31*c* can include an application specific integrated circuit (ASIC) or a system on a chip (SoC), for example, other than the field programmable gate array (FPGA).

Advantages of Method for Displaying Image of Patient Placed on Surgical Table

According to this embodiment, as described above, the method for displaying the image of the patient P placed on the surgical table 5 includes imaging the patient P placed on the surgical table 5 by the imaging device 51 provided on the arm base 50 to which the plurality of arms 60 having the medical devices 4 respectively attached thereto are attached, and displaying the patient P imaged by the imaging device 51 on the display 33*a* in real time. Accordingly, the operator (such as a nurse or a technician) can move the medical cart 3 while checking the condition of the patient P displayed on the display 33*a*.

Modified Examples

The embodiment disclosed this time must be considered as illustrative in all points and not restrictive. The scope of the present disclosure is not shown by the above description of the embodiment but by the scope of claims for patent, and all modifications (modified examples) within the meaning and scope equivalent to the scope of claims for patent are further included.

For example, while the three second trocars T2 are inserted into the patient P in the aforementioned embodiment, the present disclosure is not limited to this. The number of second trocars T2 may alternatively be two, for example.

While the first mark MK1 has a substantially circular shape in the aforementioned embodiment, the present disclosure is not limited to this. For example, the first mark MK1 may alternatively have a quadrangular shape.

While the second mark MK2 has a cross shape in the aforementioned embodiment, the present disclosure is not limited to this. For example, the second mark MK2 may alternatively have a single linear shape.

While the size of the first mark MK1 is larger than the size of the first trocar T1 displayed on the display 33*a* in the aforementioned embodiment, the present disclosure is not limited to this. For example, the size of the first mark MK1 may alternatively be the same as the size of the first trocar T1 displayed on the display 33*a*, or the first mark MK1 may alternatively have a shape (such as a point shape or a cross shape) smaller than the size of the first trocar T1.

Figure 20:
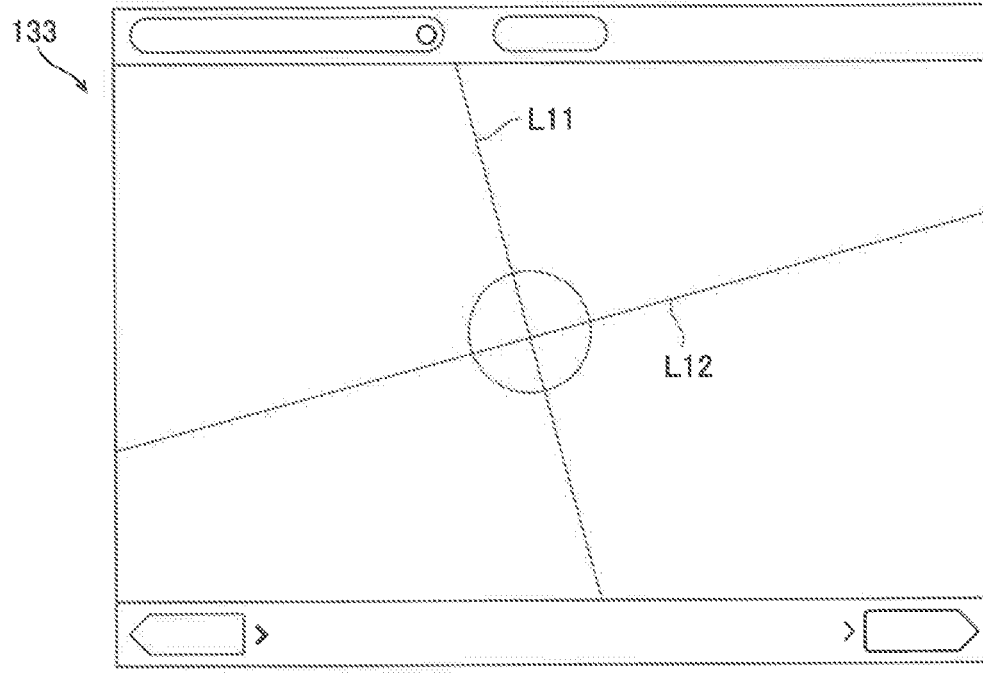
FIG. 20 is a perspective view showing a display according to a first modified example.

While the display of the first line L1 and the second line L2 on the display 33*a* is fixed on the display 33*a* in the aforementioned embodiment, the present disclosure is not limited to this. For example, as in a display 133 according to a first modified shown in FIG. 20, the display of a first line L11 and a second line L12 on the display 133 may rotate with rotation of an arm base 50, and the display of a patient P on the display 133 may be corrected to be rotated in a direction opposite to rotation of an arm base 50. That is, in the aforementioned embodiment, the image of the patient P also rotates with rotation of the arm base 50. On the other hand, on the display 133, the image of the patient P does not rotate even when the arm base 50 rotates. Thus, even when the arm base 50 is rotated, the image of the patient P displayed on the display 133 can be displayed in an orientation corresponding to the orientation of the operator (such as a nurse or a technician).

While the joystick 33*b* for operating the positioner 40 is provided in the vicinity of the display 33*a* in the aforementioned embodiment, the present disclosure is not limited to this. For example, an operation unit (such as a cross key) other than the joystick 33*b* may alternatively be provided in the vicinity of the display 33*a* to operate the positioner 40.

While the throttles 35*a* for operating movement of the medical cart 3 are provided in the vicinity of the display 33*a* in the aforementioned embodiment, the present disclosure is not limited to this. For example, an operation unit (such as a linear switch) other than the throttles 35*a* may alternatively be provided in the vicinity of the display 33*a* to operate movement of the medical cart 3.

Figure 21:
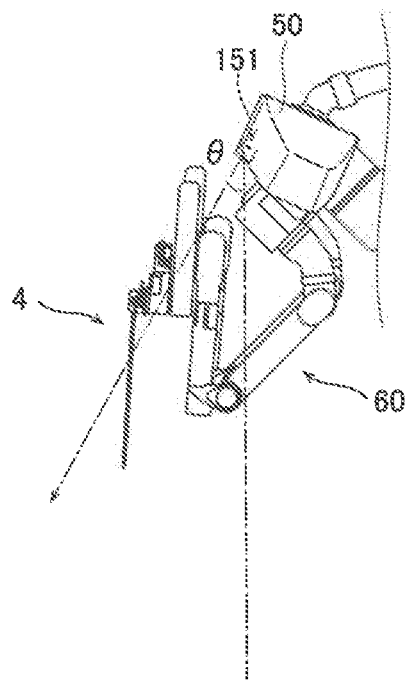
FIG. 21 is a perspective view showing an imaging device according to a second modified example.

While the imaging device 51 images the region vertically therebelow in the aforementioned embodiment, the present disclosure is not limited to this. For example, as in an imaging device 151 according to a second modified example shown in FIG. 21, in the initial stage of movement of a medical cart 3 (when the moving speed is relatively fast), the imaging device 151 may image a region obliquely forward with respect to a vertical direction, and as the medical cart 3 approaches a patient P, an angle θ with respect to the vertical direction may be gradually reduced. In this case, the angle of the imaging device 151 with respect to an arm base 50 may be variable, or the positioner 40 may be moved to change the angle θ with respect to the vertical direction in a direction (optical axis) in which the imaging device 151 is pointed.

While the four arms 60 are provided in the aforementioned embodiment, the present disclosure is not limited to this. The number of arms 60 may alternatively be three.

While each of the arm portion 61 and the positioner 40 includes a 7-axis articulated robot in the aforementioned embodiment, the present disclosure is not limited to this. For example, each of the arms 60 and the positioner 40 may alternatively include an articulated robot having an axis configuration (six axes or eight axes, for example) other than the 7-axis articulated robot.

What is claimed is:

1. A surgical robot comprising:
   a plurality of arms each configured to allow a medical device to be attached thereto;
   an arm base configured to support the plurality of arms;
   an arm base mover configured to move the arm base;
   a medical cart configured to move the arm base mover;
   an imaging device provided on the arm base, the imaging device being configured to image a patient placed on a surgical table; and
   a display configured to display, in real time, the patient imaged by the imaging device, wherein
   the display is configured to superimpose and display an image of a trocar captured by the imaging device and a mark used to align the arm base with the trocar, the trocar being configured to allow an endoscope to be inserted from a body surface of the patient, and
   the plurality of arms are aligned with a surgical location in the patient placed on the surgical table by aligning the trocar displayed on the display with the mark.

2. The surgical robot according to claim 1, wherein the display is configured to superimpose and display an image of the patient captured by the imaging device and a mark used to align the arm base with the patient.

3. The surgical robot according to claim 2, further comprising:

a magnification change button configured to enlarge or reduce an image of the mark together with the image of the patient displayed on the display.

4. The surgical robot according to claim 3, wherein
the display includes a touch panel; and
the magnification change button is configured to be displayed on the touch panel.

5. The surgical robot according to claim 1, wherein
the trocar includes a first trocar configured to allow the endoscope to be inserted thereinto, and a second trocar configured to allow the medical device other than the endoscope to be inserted thereinto; and
the mark displayed on the display includes a first mark used to align with the first trocar on the display, and a second mark used to align with the second trocar on the display.

6. The surgical robot according to claim 5, wherein
the display displays the first mark, which has a substantially circular shape, on a substantially central portion of the display; and
the second mark has a cross shape centered on the first mark having the substantially circular shape.

7. The surgical robot according to claim 6, wherein
the second trocar includes a plurality of second trocars provided on the body surface of the patient;
the display has a substantially rectangular shape; and
the second mark having the cross shape includes a substantially linear first line provided along a longitudinal direction of the display having the substantially rectangular shape, and a substantially linear second line provided along a transverse direction of the display having the substantially rectangular shape.

8. The surgical robot according to claim 7, wherein the first line and the second line displayed on the display are fixed on the display.

9. The surgical robot according to claim 1, wherein the arm base mover is configured to move the arm base such that the imaging device takes a posture to image a region vertically therebelow based on an input of mode setting to align the arm base with the patient.

10. The surgical robot according to claim 1, further comprising:
a controller including an image processing circuit configured to display an image obtained from the imaging device on the display.

11. A surgical robot comprising:
a plurality of arms each configured to allow a medical device to be attached thereto;
an arm base configured to support the plurality of arms;
an arm base mover configured to move the arm base;
a medical cart configured to move the arm base mover;
an imaging device provided on the arm base, the imaging device being configured to image a patient placed on a surgical table; and
a display configured to display, in real time, the patient imaged by the imaging device wherein
the arm base mover is configured to be controlled to move the arm base such that an orientation of the arm base corresponds to an arrangement direction of the plurality of arms determined based on an input of information on a surgical site, an input of information on a direction in which a medical manipulator is inserted into the patient, and an input of mode setting to align the arm base with the patient; and
the display is configured to display an image corrected to be rotated in a direction opposite to rotation of the arm base when movement of the arm base includes horizontal rotation of the arm base.

12. A surgical robot comprising:
a plurality of arms each configured to allow a medical device to be attached thereto;
an arm base configured to support the plurality of arms;
an arm base mover configured to move the arm base;
a medical cart configured to move the arm base mover;
an imaging device provided on the arm base, the imaging device being configured to image a patient placed on a surgical table;
a display configured to display, in real time, the patient imaged by the imaging device; and
a first operation unit configured to operate movement of the arm base mover; wherein
the first operation unit is configured to be operated and to cause the arm base mover to move the arm base on a two-dimensional plane,
the display is configured to superimpose and display an image of a trocar captured by the imaging device and a mark used to align the arm base with the trocar, the trocar being configured to allow an endoscope to be inserted from a body surface of the patient, and
the plurality of arms are aligned with a surgical location in the patient placed on the surgical table by aligning the trocar displayed on the display with the mark.

13. The surgical robot according to claim 12, further comprising:
a first enable switch configured to allow or disallow the movement of the arm base mover; wherein
the first operation unit is configured to be operated and to cause the arm base mover to move the arm base while the first enable switch is pressed.

14. The surgical robot according to claim 12, wherein the first operation unit includes a joystick.

15. The surgical robot according to claim 12, further comprising:
a second operation unit configured to operate movement of the medical cart.

16. The surgical robot according to claim 15, wherein the second operation unit includes a handle including a throttle configured to be gripped and rotated by an operator to cause the medical cart to move.

17. The surgical robot according to claim 15, further comprising:
a second enable switch configured to allow or disallow the movement of the medical cart; wherein
the second operation unit is configured to be operated and to cause the medical cart to move while the second enable switch is pressed.

18. A method for displaying, on a display of a surgical robot according to claim 12, an image of a patient placed on a surgical table, the surgical robot comprising a plurality of arms each configured to allow a medical device to be attached thereto and an arm base configured to support the plurality of arms, the method comprising:
imaging a patient placed on a surgical table by an imaging device provided on the arm base; and
displaying the patient imaged by the imaging device on the display in real time.

19. A method for aligning a plurality of arms with a surgical location in a patient placed on a surgical table, comprising:
displaying a mark on a display for aligning the plurality of arms;
capturing an image of a trocar inserted into a body surface of the patient at a surgical location, the trocar configured to allow a medical device attached to one of the plurality of arms to be inserted thereinto;

displaying the captured image of the trocar on the display, the display of captured image of the trocar superimposed with the mark, and aligning the one of the plurality of arms with the surgical location in the patient placed on the surgical table by aligning the display of the trocar with the display of the mark, wherein displaying the mark and the captured image of the trocar comprises superimposing and displaying the image of a trocar and the mark used to align the arm base with the trocar, and aligning the plurality of arms with a surgical location in the patient placed on the surgical table by aligning the trocar displayed on the display with the mark.

\* \* \* \* \*